United States Patent [19]

Hofheinz

[11] Patent Number: 4,515,790
[45] Date of Patent: May 7, 1985

[54] ANTIPROTOZOAL 2-NITROIMIDAZOLE COMPOUNDS

[75] Inventor: Werner Hofheinz, Bottmingen, Switzerland

[73] Assignee: Hoffmann-La Roche Inc., Nutley, N.J.

[21] Appl. No.: 444,106

[22] Filed: Nov. 24, 1982

[30] Foreign Application Priority Data

Nov. 30, 1981 [CH]  Switzerland .......................... 7657/81
Sep. 28, 1982 [CH]  Switzerland .......................... 5701/82

[51] Int. Cl.³ .................... A01N 43/50; A01N 43/60; A01N 43/84; C07D 413/12
[52] U.S. Cl. .................................. 514/234; 514/252; 514/326; 514/397; 514/398; 544/139; 544/370; 546/210; 548/336; 548/339
[58] Field of Search .............. 548/339, 336; 546/210; 544/139, 370; 424/273 R, 267, 248.54, 250

[56] References Cited

U.S. PATENT DOCUMENTS 3,954,789  5/1976  Cavalleri et al. ................... 548/339
3,987,053 10/1976  Cavalleri et al. ................... 548/338
4,105,763  8/1978  Winkelmann et al. .......... 548/339 X

FOREIGN PATENT DOCUMENTS 76007    5/1977  Luxembourg ...................... 548/339
1579270 11/1980  United Kingdom ............... 548/339

Primary Examiner—Richard A. Schwartz
Attorney, Agent, or Firm—Jon S. Saxe; George M. Gould; John J. Maitner

[57] ABSTRACT

2-Nitroimidazoles having protozoocidal activity of the formula

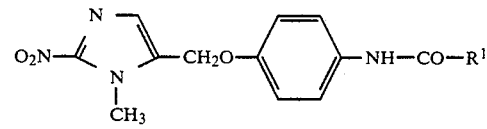

wherein $R^1$ is 1-methyl-2-pyrrolidinyl or a group $-CH_2-NR^2R^3$ in which $R^2$ and $R^3$ each represent $C_{1-4}$-alkyl or $-NR^2R^3$ is the residue of a five-membered or six-membered saturated heterocyclic ring system which optionally contains an additional nitrogen or oxygen atom in the ring, physiologically acceptable acid addition salts thereof, processes for their preparation, and pharmaceutical compositions containing these compounds are described.

11 Claims, No Drawings

ANTIPROTOZOAL 2-NITROIMIDAZOLE COMPOUNDS

DETAILED DESCRIPTION OF THE INVENTION

The present invention relates to novel 2-nitroimidazoles of the formula

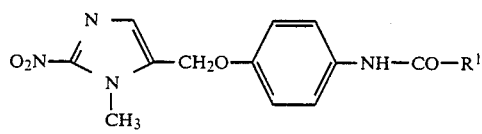
I wherein $R^1$ is 1-methyl-2-pyrrolidinyl or a group —$CH_2$—$NR^2R^3$ in which $R^2$ and $R^3$ each represent $C_{1-4}$-alkyl or —$NR^2R^3$ is the residue of a five-membered or six-membered saturated heterocyclic ring system which optionally contains a further nitrogen or oxygen atom in the ring, and physiologically acceptable acid addition salts thereof.

This invention is also directed to processes for the preparation of the compounds of formula I, as well as pharmaceutical compositions which contain, as the active ingredient, a compound of formula I, and methods for their use. The compounds exhibit protozoocidal activity.

As used throughout this application, the term $C_{1-4}$-alkyl encompasses both straight-chain or branched-chain groups, e.g. methyl, ethyl, propyl, isopropyl, butyl, and t-butyl. The preferred groups are methyl and ethyl. Examples of five-membered or six-membered heterocyclic ring systems which optionally contain a further nitrogen or oxygen atom in the ring are pyrrolidine, piperidine, piperazine, and morpholine.

The 2-nitroimidazole compounds of formula I are prepared by one of the procedures described hereinafter.

Procedure A. Reacting a compound of the formula

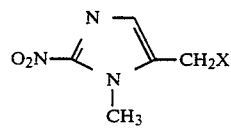
II wherein X is hydroxy, chlorine, bromine, or iodine, with a compound of the formula

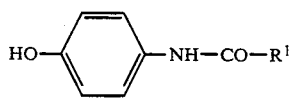
III wherein $R^1$ is as described above.

Procedure B. Reacting a 2-halo-α-(1-methyl-2-nitroimidazol-5-yl)-p-acetanisidide with a compound of the formula $HNR^2R^3$ in which $R^2$ and $R^3$ are as described above.

Procedure C. Reacting α-(1-methyl-2-nitroimidazol-5-yl)-p-anisidine with a compound of the formula $R^1$-COOH in which $R^1$ is as described above or a reactive derivative thereof and, if desired, converting a compound of formula I obtained into a physiologically acceptable acid addition salt.

The above-noted procedures, i.e., A, B, and C are condensation reactions which can be carried out within the framework of usual conditions which are familiar to a person skilled in the art, i.e., in one of the known inert solvents, at temperatures between room temperature and the reflux temperature of the reaction mixture, and if desired, in the presence of a condensation agent.

In procedure A, wherein X is hydroxy, a preferred condensation agent is an azodicarboxylic acid ester, e.g. diisopropyl or diethyl azodicarboxylate, in combination with triphenylphosphine and suitable inert solvents are ethers, preferably dioxane and tetrahydrofuran. When X is halogen and in procedure B no condensation agent is necessary and the solvent is not critical; however, preferred solvents are ethanol and dimethyl formamide.

In procedure C condensation and activating agents can be used which are well-known in peptide chemistry. Preferred condensation agents are 2-fluoro- or 2-chloro-1-methyl-pyridinium salts, 2-chloro-3-alkyl-benzoxazolium or -benzthiazolium salts, in the presence of a base, such as triethyl amine. The reaction is preferably carried out in an aprotic polar solvent, such as acetonitrile or dimethyl formamide. Reactive derivatives of compounds of formula $R^1$-COOH used in procedure C include, for example, acid halides and anhydrides.

The 2-nitroimidazole compounds of formula I of the present invention exhibit protozoocidal, especially trypanosomicidal, activity. Compared with known compounds which have recognized good trypanosomicidal activity such as, for example, pentamidine or suramin, the compounds of formula I exhibit excellent fluid passability. When compared with known 2-nitroimidazole compounds which exhibit the same activity such as, for example, benznidazole or misonidazole, the compounds of formula I exhibit substantially increased activity against African trypanosomes, e.g. Trypanosoma rhodesiense which causes sleeping sickness (see Table 1).

In the field of veterinary medicine, the compounds of formula I of the present invention are useful in the treatment of trypanosome diseases. Prominent diseases of this type include Nagana (caused by T. congolense, T. vivax, T. brucei), surra (caused by T. evansi), and dourine (t. equiperdum).

TABLE 1

| Compound | $ED_{50}$ [mg/kg], T. rhodesiense p.o. |
| --- | --- |
| Misonidazole | 400 |
| Benznidazole | 400 |
| 2-(Dimethylamino)-α-(1-methyl-2-nitroimidazol-5-yl)-p-acetanisidide | 3 |
| 2-(Diethylamino)-α-(1-methyl-2-nitroimidazol-5-yl)-p-acetanisidide | 17 |
| 2-(Dibutylamino)-α-(1-methyl-2-nitroimidazol-5-yl)-p-acetanisidide | 90 |
| α-(1-Methyl-2-nitroimidazol-5-yl)-1-pyrrolidine-p-acetanisidide | 2.7 |
| α-(1-Methyl-2-nitroimidazol-5-yl)-1-piperidine-1-acetanisidide | 55 |
| α-(1-Methyl-2-nitroimidazol-5-yl)-4-morpholine-p-acetanisidide | 30 |
| (2S)-1-Methyl-α-(1-methyl-2-nitroimidazol-5-yl)-pyrrolidine-carboxy-p-anisidide | 18 |

The compounds of formula I of the present invention are, therefore, useful as medicaments, namely for the prophylaxis and therapy of illnesses caused by protozoa, especially trypanosomes, such as sleeping sickness. The compounds can be administered in the form of solid or liquid pharmaceutical compositions in combination with pharmaceutically acceptable organic or inorganic inert carrier materials suitable for oral or parenteral administration as well as the usual adjuvant substances.

Suitable art-recognized pharmaceutically acceptable inert carrier materials useful in the preparation of the compositions of the present invention include, for example, water, gelatin, gum arabic, lactose, starch, talc, magnesium stearate, vegetable oils, polyalkyleneglycols, and the like. The pharmaceutical compositions of the present invention may also contain art-recognized adjuvants, for example, preservatives, stabilizers, wetting or emulsifying agents, agents for flavor improvement, salts to adjust osmotic pressure, buffers, and the like. The pharmaceutical compositions can be prepared by conventional procedures recognized in the art.

Compositions containing the 2-nitroimidazole compounds of formula I can be utilized in the therapeutic treatment of protozoal infection in a considerable range of dosage depending on the individual clinical condition. Factors which may influence the dosage range include the type and severity of the infection and the activity of the specific compound administered. Generally, however, it is contemplated that a sufficient amount of such a composition be administered to provide about 1–10 mg/kg body weight per day, administered in one or more individual doses and for up to 10 days. Unit dosage forms of the compositions of the present invention generally contain from about 50 to about 1000 mg of a compound of formula I. For use in veterinary medicine, similar dosage forms can be employed.

The compounds of formula I of the present invention can be present in the pharmaceutical preparations in the form of their acid addition salts with known physiologically compatible acids. Examples of such acid addition salts include hydrochloric acid, sulfuric acid, phosphoric acid, acetic acid, citric acid, or tartaric acid, and the like. These salts can be prepared by reacting the compounds of formula I with the desired acid by conventional procedures recognized in the art.

The preparation of the compounds of formula I is illustrated by the following Examples.

EXAMPLE 1

78.5 g of 1-methyl-2-nitroimidazole-5-methanol were suspended in 1.5 l of anhydrous tetrahydrofuran. After the addition of 102 g of p-chloroacetylaminophenol and 144 g of triphenylphosphane, the mixture was cooled to 10° C. and a solution of 111 g of diisopropyl azodicarboxylate in 750 ml of anhydrous tetrahydrofuran was added thereto with vigorous stirring within 20 minutes, the temperature being held at 10°–12° C. by means of an ice-bath. The mixture was stored in a refrigerator overnight and the crystalline precipitate was filtered off under suction. Recrystallization from 2 l of acetonitrile, yielded 90.9 g (56.6%) of pure 2-chloro-α-(1-methyl-2-nitroimidazol-5-yl)-p-acetanisidide, m.p. 192°–194° C. (decomposition).

32 ml of a 3.68 molar solution of dimethylamine in ethanol were added to a suspension of 20 g of the foregoing anisidide in 500 ml of ethanol. The mixture was refluxed for 5 hours, concentrated to dryness under reduced pressure and taken up with 1 l of methylene chloride and 400 ml of water. The mixture was adjusted to pH 7 with sodium bicarbonate. The organic phase was then separated, washed with a small amount of water and evaporated. Crystallization of the residue from 200 ml of isopropanol yielded 16.6 g (82%) of 2-(dimethylamino)-α-(1-methyl-2-nitroimidazol-5-yl)-p-acetanisidide, m.p. 128°–129° C.

15 g of 2-(dimethylamino)-α-(1-methyl-2-nitroimidazol-5-yl)-p-acetanisidide were dissolved in 300 ml of hot ethanol. 12 ml of 4.1N ethanolic hydrochloric acid were added dropwise thereto while stirring. The mixture was cooled in an ice-bath and 250 ml of diethyl ether were added thereto. After allowing the mixture to stand in a refrigerator overnight, the precipitated hydrochloride was filtered off under suction, washed with diethyl ether and dried in vacuo to yield 16.4 g of 2-(dimethylamino)-α-(1-methyl-2-nitroimidazol-5-yl)-p-acetanisidide hydrochloride, m.p. 193°–194° C. (decomposition).

EXAMPLE 2

7 g of 2-chloro-α-(1-methyl-2-nitroimidazol-5-yl)-p-acetanisidide and 3.8 g of pyrrolidine were heated under reflux for 5 hours in 200 ml of ethanol. The mixture was concentrated to about 50 ml and cooled. Recrystallization of the precipitate from acetonitrile yielded 5.9 g (76%) of α-(1-methyl-2-nitroimidazol-5-yl)-1-pyrrolidine-p-acetanisidide, m.p. 141°–143° C.

15 g of α-(1-methyl-2-nitroimidazol-5-yl)-1-pyrrolidine-p-acetanisidide were dissolved in 350 ml of hot ethanol. 11 ml of 4.1N ethanolic hydrochloric acid were added dropwise thereto while stirring, the mixture was cooled in an ice-bath and 250 ml of diethyl ether were added thereto. After leaving to stand in a refrigerator overnight, the precipitated hydrochloride was filtered off under suction, washed with diethyl ether and dried in vacuo to yield 15.4 g of α-(1-methyl-2-nitroimidazol-5-yl)-1-pyrrolidine-p-acetanisidide hydrochloride, m.p. 209°–210° C. (decomposition).

EXAMPLE 3

In a manner analogous to Example 2, from 4.6 g of piperidine there were obtained 6.1 g (75%) of α-(1-methyl-2-nitroimidazol-5-yl)-1-piperidine-p-acetanisidide, m.p. 162°–163° C.

EXAMPLE 4

In a manner analogous to Example 2, from 3.95 g of diethylamine there were obtained 5 g (64%) of 2-(diethylamino)-α-(1-methyl-2-nitroimidazol-5-yl)-p-acetanisidide, m.p. 106°–108° C. (from toluene).

EXAMPLE 5

In a manner analogous to Example 2, from 3.24 g of 2-chloro-α-(1-methyl-2-nitroimidazol-5-yl)-p-acetanisidide and 2.18 g of morpholine there were obtained 3.3 g (83%) of α-(1-methyl-2-nitroimidazol-5-yl)-4-morpholine-p-acetanisidide, m.p. 154°–156° C. (from methanol).

EXAMPLE 6

A suspension of 30 g of 1-methyl-2-nitroimidazole-5-methanol, 22 g of 4-aminophenol and 55 g of triphenylphosphane in 600 ml of anhydrous tetrahydrofuran was treated dropwise with vigorous stirring within 20 minutes with a solution of 42.5 g of diisopropyl azodicarboxylate in 300 ml of anhydrous tetrahydrofuran. The mixture was maintained at a temperature of 20°–24° C. by external cooling. After 2 hours, the clear solution obtained was evaporated under reduced pressure and the residue was boiled briefly with a mixture of 125 ml of methylene chloride and 125 ml of ethyl acetate to yield 24.4 g (52%) of crystalline α-(1-methyl-2-nitroimidazol-5-yl)-p-anisidine, m.p. 168°–170° C.

A solution of 4.14 g of N-methyl-L-proline and 6.2 g of the foregoing anisidine in 250 ml of acetonitrile was treated with 12.5 ml of triethylamine and subsequently with 8.5 g of 2-fluoro-1-methylpyridinium tosylate. The mixture was heated under reflux for 1 hour, the solvent was removed under reduced pressure and the residue was partitioned between 200 ml of ethyl acetate and 200 ml of water. The aqueous phase was adjusted to pH 10 with sodium hydroxide and extracted three times with 100 ml of ethyl acetate each time. The combined extracts were evaporated. The residue was filtered over 28 g of silica gel with acetone/toluene (1:1, v/v). After a forerun of 350 ml, from the next 2000 ml of the eluate there were obtained 8.1 g of (2S)-1-methyl-α-(1-methyl-2-nitroimidazol-5-yl)-pyrrolidine-carboxy-p-anisidide in the form of an oily crude product. Recrystallization from ether yielded 2.5 g (27%) of pure product, m.p. 106°–107° C.; $[\alpha]_D^{25} = -66.5°$ (c=1% in methanol).

EXAMPLE 7

A lithium diisopropylamine solution (prepared from 65 ml of a 2.2 molar solution of butyl lithium in hexane and 14.5 g of diisopropylamine in 150 ml of tetrahydrofuran) was added dropwise at a temperature of −60° C. within 15 minutes to a solution of 22 g of 1-methyl-2-nitroimidazole-5-methanol in 300 ml of tetrahydrofuran and 150 ml of dimethylformamide. The mixture was stirred at −60° C. for 30 minutes and treated with 28 g of p-toluenesulphonyl chloride in 150 ml of tetrahydrofuran. After removing the cooling, warming to room temperature and adding 300 ml of ice/water, the mixture was extracted three times with 300 ml of ethyl acetate each time. The combined extracts were washed with 150 ml of saturated sodium chloride solution and evaporated under reduced pressure. The residue was purified on 800 g of silica gel with ethyl acetate/dichloromethane (1:3, v/v). After a forerun of 1.5 l, the next 1.5 l were collected and evaporated. Recrystallization from 70 ml of toluene yielded 12 g (50%) of 5-(chloromethyl)-1-methyl-2-nitroimidazole, m.p. 100°–101° C.

2.9 ml of a 1.98 molar solution of sodium tert.amylate in toluene were added at −10° C. to a solution of 1.26 g of 4'-hydroxy-1-pyrrolidine-acetanilide in 10 ml of dimethylformamide. 1 g of 5-(chloromethyl)-1-methyl-2-nitroimidazole was subsequently added and the mixture was stirred at −10° C. for 3 hours. 100 ml of water were added in order to isolate the product. Recrystallization of the product from 13 ml of acetonitrile yielded 0.42 g (21%) of α-(1-methyl-2-nitroimidazol-5-yl)-1-pyrrolidine-p-acetanisidide, m.p. 141°–143° C.

EXAMPLE 8

0.17 g of diethyl azodicarboxylate in 1.5 ml of tetrahydrofuran was added dropwise while cooling with ice and vigorous stirring to a suspension of 0.14 g of 1-methyl-2-nitroimidazole-5-methanol, 0.22 g of 4'-hydroxy-1-pyrrolidine-acetanilide and 0.26 g of triphenylphosphane in 3 ml of absolute tetrahydrofuran. The mixture was stirred at room temperature for 3 hours and the resulting clear solution was evaporated under reduced pressure. The crude product was purified by chromatography on a silica gel column. By-products were firstly eluted with ethyl acetate, while the main product was obtained by elution with dichloromethane/methanol (9:1, v/v). Evaporation of the solvent mixture and crystallization from 1 ml of acetonitrile yielded 0.115 g (36%) of α-(1-methyl-2-nitroimidazol-5-yl)-1-pyrrolidine-p-acetanisidide, m.p. 140°–142° C.

The following Examples illustrate pharmaceutical compositions containing the compounds of formula I and physiologically compatible acid addition salts thereof:

EXAMPLE A

Tablets containing the following ingredients were prepared by conventional procedures:

| | |
|---|---|
| 2-(Dimethylamino)-α-(1-methyl-2-nitroimidazol-5-yl)-p-acetanisidide hydrochloride | 100 mg |
| Lactose | 192 mg |
| Maize starch | 80 mg |
| Hydrolyzed maize starch | 20 mg |
| Calcium stearate | 8 mg |
| | 400 mg |

EXAMPLE B

Tablets containing the following ingredients were prepared by conventional procedures:

| | |
|---|---|
| α-(1-Methyl-2-nitroimidazol-5-yl)-1-pyrrolidine-p-acetanisidide hydrochloride | 50 mg |
| Lactose | 194 mg |
| Pre-gelatinized maize starch | 150 mg |
| Calcium stearate | 6 mg |
| | 400 mg |

EXAMPLE C

An injectable solution containing the following ingredient was prepared by conventional procedures:

| | Per ml |
|---|---|
| 2-(Dimethylamino)-α-(1-methyl-2-nitroimidazol-5-yl)-p-acetanisidide | 5.1 mg |
| Propylene glycol | 0.4 ml |
| Benzyl alcohol (benzaldehyde-free) | 0.015 ml |
| Ethanol (anhydrous) | 0.10 ml |
| Sodium benzoate | 48.8 mg |
| Benzoic acid | 1.2 mg |
| Water (for injection) q.s. | 1.0 ml |

I claim:

1. A 2-nitroimidazole compound of the formula:

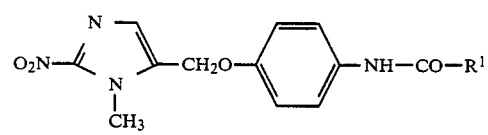

wherein $R^1$ is 1-methyl-2-pyrrolidinyl or a group —CH$_2$—NR$^2$R$^3$ in which $R^2$ and $R^3$ each represent C$_{1-4}$-alkyl or —NR$^2$R$^3$ is the residue of a five-membered or six-membered saturated heterocyclic ring system selected from the group consisting of pyrrolidine, piperidine, piperazine and morpholine or a physiologically acceptable acid addition salt thereof.

2. The compound of claim 1 wherein said compound is
1-Methyl-α-(1-methyl-2-nitroimidazol-5-yl)-pyrrolidine-carboxy-p-anisidide.

3. The compound of claim 1 wherein said compound is
2-(Dimethylamino)-α-(1-methyl-2-nitroimidazol-5-yl)-p-acetanisidide.

4. The compound of claim 1 wherein said compound is
2-(Dimethylamino)-α-(1-methyl-2-nitroimidazol-5-yl)-p-acetanisidide hydrochloride.

5. The compound of claim 1 wherein said compound is
2-(Diethylamino)-α-(1-methyl-2-nitroimidazol-5-yl)-p-acetanisidide.

6. The compound of claim 1 wherein said compound is
α-(1-Methyl-2-nitroimidazol-5-yl)-1-pyrrolidine-p-acetanisidide.

7. The compound of claim 1 wherein said compound is
α-(1-Methyl-2-nitroimidazol-5-yl)-1-pyrrolidine-p-acetanisidide hydrochloride.

8. The compound of claim 1 wherein said compound is
α-(1-Methyl-2-nitroimidazol-5-yl)-1-piperidine-p-acetanisidide.

9. The compound of claim 1 wherein said compound is
α-(1-Methyl-2-nitroimidazol-5-yl)-4-morpholine-p-acetanisidide.

10. A pharmaceutical composition for the treatment of protozoal infections comprising a pharmaceutically acceptable inert carrier and a therapeutically effective amount of a compound of the formula

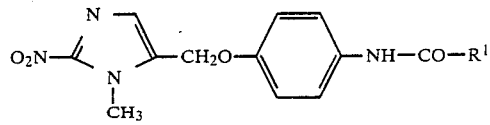

wherein $R^1$ is 1-methyl-2-pyrrolidinyl or a group $—CH_2—NR^2R^3$ in which $R^2$ and $R^3$ each represent $C_{1-4}$-alkyl or $—NR^2R^3$ is the residue of a five-membered or six-membered saturated heterocyclic ring system selected from the group consisting of pyrrolidine, piperidine, piperazine and morpholine, or a physiologically acceptable acid addition salt thereof.

11. A method for the treatment of protozoal infections which comprises administering to a host requiring such treatment an effective amount of a compound of the formula

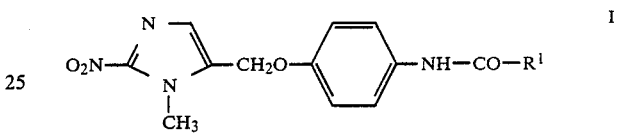

wherein $R^1$ is 1-methyl-2-pyrrolidinyl or a group $—CH_2—NR^2R^3$ in which $R^2$ and $R^3$ each represent $C_{1-4}$-alkyl or $—NR^2R^3$ is the residue of a five-membered or six-membered saturated hetrocyclic ring system selected from the group consisting of pyrrolidine, piperidine, piperzine and morpholine, or a physiologically acceptable acid addition salt thereof.

* * * * *